United States Patent [19]

Wang et al.

[11] Patent Number: 5,028,668

[45] Date of Patent: Jul. 2, 1991

[54] ADDUCTS OF METABROMINATED PHENOLS AND POLYFUNCTIONAL EPOXIDES

[75] Inventors: Chun S. Wang, Lake Jackson, Tex.; Abel Mendoza, Midland, Mich.

[73] Assignee: The Dow Chemical Company, Midland, Mich.

[21] Appl. No.: 549,177

[22] Filed: Jul. 6, 1990

Related U.S. Application Data

[62] Division of Ser. No. 440,149, Nov. 22, 1989, Pat. No. 4,975,500, which is a division of Ser. No. 851,996, Apr. 14, 1986, Pat. No. 4,914,185.

[51] Int. Cl.$^5$ ............................................. C08G 59/14
[52] U.S. Cl. ................................... 525/481; 525/482; 525/523; 525/534; 528/102; 528/98
[58] Field of Search ............... 525/481, 482, 523, 534; 528/102, 98

[56] References Cited

U.S. PATENT DOCUMENTS

| | | | |
|---|---|---|---|
| 3,723,335 | 3/1973 | Tanaka et al. | 528/102 |
| 3,775,355 | 11/1973 | Jellinek et al. | 260/37 EP |
| 4,358,577 | 11/1982 | McCrary et al. | 528/102 |
| 4,501,787 | 2/1985 | Marchetti et al. | 428/236 |
| 4,559,395 | 12/1985 | Jackson | 528/102 |
| 4,567,242 | 1/1986 | Nishibori et al. | 525/534 |
| 4,604,317 | 8/1986 | Berman et al. | 528/102 |
| 4,914,185 | 4/1990 | Wang et al. | 528/102 |
| 4,975,500 | 12/1990 | Wang et al. | 528/102 |

*Primary Examiner*—Earl Nielsen
*Assistant Examiner*—Frederick Krass

[57] ABSTRACT

Adducts of metabrominated monophenols such as 3,5-dibromo-2,4,6-trimethylphenol and multifunctional epoxides such as cresol-formaldehyde epoxy novolac resins are disclosed to be useful in formulations for encapsulating electronic components.

5 Claims, No Drawings

ADDUCTS OF METABROMINATED PHENOLS AND POLYFUNCTIONAL EPOXIDES

CROSS-REFERENCE TO RELATED APPLICATION

This application is a division of application Ser. No. 07/440,149 filed Nov. 22, 1989, now U.S. Pat. No. 4,975,500 which is a division of application Ser. No. 06/851,996, filed Apr. 14, 1986, (now U.S. Pat. No. 4,914,185) which applications are incorporated herein by reference in their entirety.

BACKGROUND OF THE INVENTION

The present invention pertains to novel adducts of metabrominated phenols and polyfunctional epoxy resins and formulations containing same.

Electrical laminates have been encapsulated with fire resistant encapsulating components containing as the resin portion thereof blends of cresol-formaldehyde novolac epoxy resins and the diglycidyl ether of tetrabromobisphenol A. While the formulations prepared from these blends are adequate, the bromine tends to hydrolylze which ultimately leads to corrosion of the electronic part which is encapsulated therein. It is therefore desirable to have formulations for encapsulating electrical components in which the formulation contains a brominated resin in which the bromine does not hydrolyze as readily as in the diglycidyl ether of tetrabromobisphenol A.

The present invention provides an epoxy resin for use in electrical encapsulation formulations which results in encapsulated objects having an improvement in one or more of the properties such as, moisture absorption, hydrolyzable bromide, dielectric constant and the like.

SUMMARY OF THE INVENTION

One aspect of the present invention pertains to a composition which comprises an adduct prepared by reacting (A) a metabrominated monophenol and (B) a multifunctional polyepoxide having an average of more than two epoxide groups per molecule; wherein components (A) and (B) are employed in quantities which provide a ratio of phenolic hydroxyl groups to epoxide groups of from about 0.05:1 to about 0.5:1, preferably from about 0.07:1 to about 0.35:1, most preferably from about 0.1:1 to about 0.2:1.

Another aspect of the present invention pertains to a mixture comprising (A) a glycidyl ether of a metabrominated monophenol and (B) a polyepoxide having an average of more than one vicinal epoxide group per molecule; wherein components (A) and (B) are employed in quantities which provide the resultant mixture with a bromine content of from about 2 to about 20, preferably from about 5 to about 15, most preferably from about 7 to about 12 percent by weight.

Another aspect of the present invention pertains to an encapsulating formulation which comprises (I) the aforementioned adduct or the aforementioned mixture; and (II) a curing amount of a curing agent for component (A).

A further object of the present invention pertains to an electrical component encapsulated with the aforementioned encapsulating formulation.

DETAILED DESCRIPTION OF THE INVENTION

Any multifunctional epoxy resin which has an average vicinal epoxide functionality of greater than 1 or 2 as indicated can be employed in the present invention. It is preferred, however, that the epoxy resin have an epoxide functionality of greater than about 3 where multifunctional epoxy resins are employed. Suitable epoxy resins include, for example, those represented by the following formulas I, II, III, IV and V or a combination thereof

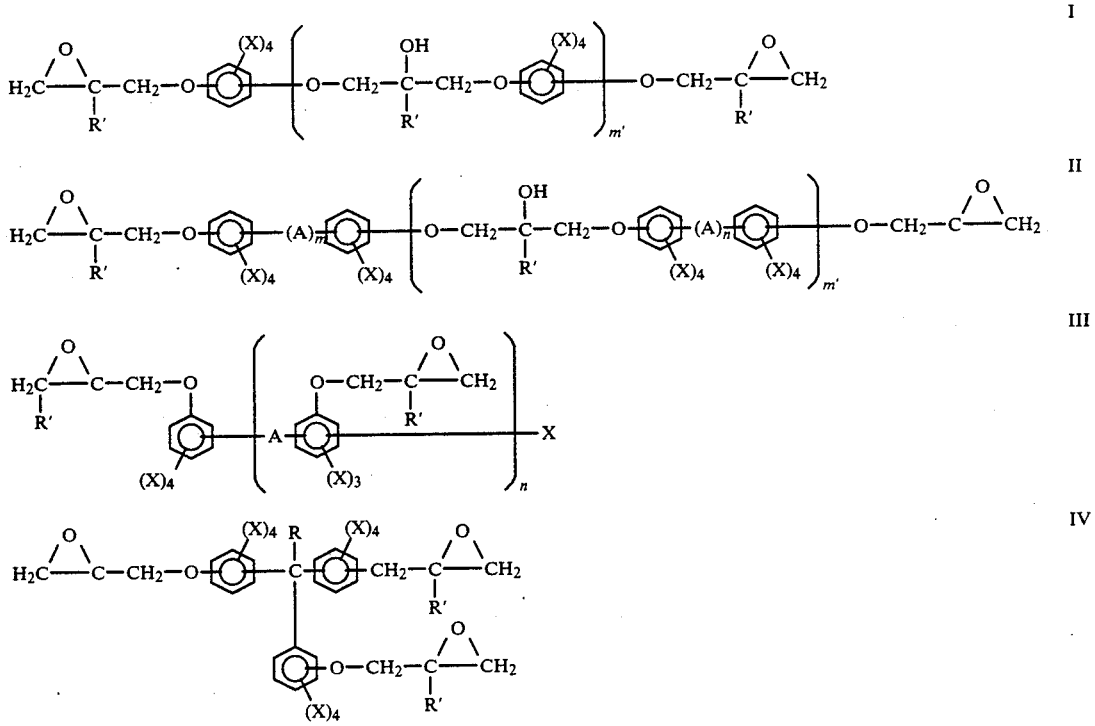

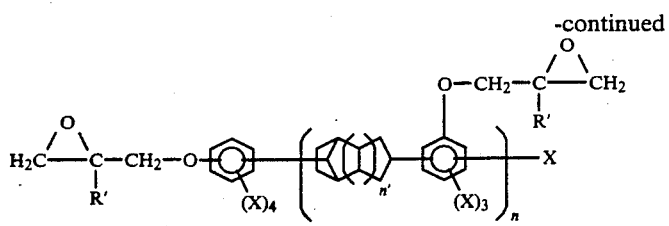

wherein each A is independently a divalent hydrocarbyl group having from 1 to about 12, preferably from about 1 to about 6, most preferably from about 1 to about 3 carbon atoms; R is hydrogen or a monovalent hydrocarbyl group having from 1 to about 12, preferably from about 1 to about 6, most preferably from about 1 to about 3 carbon atoms; each R' is independently hydrogen or an alkyl group having from 1 to about 4 carbon atoms; each X is independently hydrogen, a monovalent hydrocarbyl group or hydrocarbyloxy group having from 1 to about 12, preferably from about 1 to about 6, most preferably from about 1 to about 3 carbon atoms or a halogen atom; m has a value of zero or 1; m' has a value from zero to about 10, preferably from about 0.03 to about 6, most preferably from about 0.03 to about 3; n has an average value from about 1.01 to about 12, preferably from about 1 to about 6 and n' has an average value from about 1 to about 12, preferably from about 1 to about 6.

The term hydrocarbyl as employed herein includes, alkyl, cycloalkyl, aryl, aralkyl, alkaryl, alkenyl and the like. Likewise, the term hydrocarbyloxy as employed herein includes, alkyloxy, cycloalkyloxy, aryloxy, aralkyloxy, alkaryloxy, alkenyloxy and the like.

Particlularly suitable epoxy resins which can be employed herein are the cresol-formaldehyde epoxy novolac resins.

Suitable metabrominated phenols which can be employed herein include, for example, those represented by the following formula VI

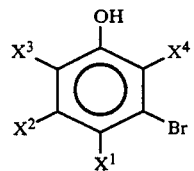

wherein $X^1$, $X^3$ and $X^4$ are independently hydrogen or a monovalent hydrocarbyl or hydrocarbyloxy group having from 1 to about 12, preferably from about 1 to about 6, most preferably from about 1 to about 4, carbon atoms and $X^2$ is hydrogen, bromine or a monovalent hydrocarbyl group or hydrocarbyloxy group having from 1 to about 12, preferably from about 1 to about 6, most preferably from about 1 to about 4, carbon atoms. Particularly suitable metabrominated phenols include, for example, 3,5-dibromo-2,4,6-trimethylphenol, 3-bromo-2,4,6-trimethylphenol, 3,5-dibromophenol, 3-bromophenol, 3-bromo-2,4,5,6-tetramethylphenol, 3,5-dibromo-2,4,6-triethylphenol, 3-bromo-2,4,6-triethylphenol, combinations thereof and the like.

The metabrominated phenols can be prepared by the bromination of the corresponding non-brominated phenols.

The adducts of the present invention can be cured with any epoxy resin curing agent such as, for example, primary and secondary amines, polycarboxylic acids and anhydrides thereof, materials containing an average of more than one aromatic hydroxyl group per molecule, amides, sulfones, sulfonamides, polyhydric phenols, phenol-aldehyde novolac resins, combinations thereof and the like. Particularly suitable curing agents include the phenol-aldehyde novolac resins, particularly the phenol-formaldehyde novolac resins.

The curing agent can be employed in amounts which correspond to either less than or greater than stoichiometric quantities, i.e. from less than one equivalent of curing agent per epoxide equivalent to more than one equivalent of curing agent per epoxide equivalent.

In addition to the epoxy resin adduct and the curing agent therefor, the encapsulating formulations of the present invention can also contain, if desired, fillers, pigments, dyes, flow control agents, surfactants, leveling agents, flame retardant agents, reinforcing materials, plasticizers, extenders, mold release agents, combinations thereof and the like.

The following examples are illustrative of the present invention.

EXAMPLE 1

Four hundred grams (2 epoxy equiv.) of a cresol-formaldehyde epoxy novolac resin having an average functionality of 5.5 and containing 92 parts per million (ppm) hydrolyzable chloride and 882 ppm total chloride by weight was dissolved in 400 g of a 75/25 by weight mixture of methyl ethyl ketone/toluene. Then, 88 g (0.299 phenolic hydroxyl equiv.) of 3,5-dibromo-2,4,6-trimethylphenol and 1.2 g of polyethylene glycol having an average molecular weight of about 400 were added to the solution and the solution was heated to 80° C. with stirring. Then, 2.8 g of 45% aqueous potassium hydroxide (2 equiv. of kOH per equiv. of Cl) was added all at once and the reaction mixture was maintained at 80° C. for 6 hours (21,600 s). The reaction mixture was diluted to 20% non-volitiles by weight with the aforementioned 75/25 methyl ethyl ketone/toluene solvent mixture, neutralized with carbon dioxide and then washed several times with water to remove the KCl. The organic phase from the washes was placed in a rotary evaporator under a full vacuum and heated at 160° C. to completely remove the solvent. A yellow solid having a viscosity of 363 centistokes at 150° C., 9.95 wt. % bromine, 11 ppm hydrolyzable chloride and 556 ppm total chloride was obtained.

EXAMPLE 2

A 3.6 functional phenol-formaldehyde epoxy novolac (100 grams, 0.57 epoxy equiv.) containing 68 ppm hydrolyzable chloride and 1136 ppm total chloride was reacted with 25 grams (0.085 phenolic hydroxyl equiv.) of 3,5-dibromo-2,4,6-trimethylphenol by the procedure of Example 1. The resultant product was a yellow solid containing 10.5 weight percent bromine, 7 ppm hydrolyzable chloride and 744 ppm total chloride.

EXAMPLE 3

A triglycidyl ether of trihydroxyphenyl methane having an average functionality of 3.4 (100 grams, 0.645 epoxy equiv.) containing 176 ppm hydrolyzable chloride and 1349 ppm total chloride was reacted with 22 grams (0.075 phenolic equiv.) of 3,5-dibromo-2,4,6-trimethylphenol by the procedure of Example 1. The resultant product was a yellow solid containing 9.58 weight percent bromine, 11 ppm hydrolyzable chloride and 972 ppm total chloride.

EXAMPLE 4

A dicyclopentadiene-phenol epoxy novolac having an average functionality of 3.2 (100 grams, 0.441 epoxy equiv.) containing 286 ppm hydrolyzable chloride and 2496 ppm total chloride was reacted with 25 grams (0.085 phenolic equiv.) of 3,5-dibromo-2,4,6-trimethylphenol by the procedure of Example 1. The resultant product was an orange solid containing 8.6 weight percent bromine, 16 ppm hydrolyzable chloride and 643 ppm total chloride.

EXAMPLE 5

A. Epoxidation of 3,5-dibromo-2,4,6-trimethylphenol

To a 2-liter reaction vessel equipped with temperature and pressure control and indicating means, a means for the continuous addition of aqueous sodium hydroxide, a means for condensing and separating water from a co-distillate mixture of water, solvent and epichlorohydrin and means for returning the solvent and epichlorohydrin to the reaction vessel was added 315.5 (1.07 phenolic hydroxyl equiv.) of 3,5-dibromo-2,4,6-trimethylphenol and 695 g (7.517 moles) of epichlorohydrin and 464 g of the methyl ether of propylene glycol (1-methyl-2-hydroxy-propane) as a solvent. After stirring at room temperature and atmospheric pressure to thoroughly mix the contents, the temperature was raised to 55° C. and the pressure was reduced to 105 mm Hg absolute. To the resultant solution was continuously added 85.9 g (1.0739 moles of 50% aqueous sodium hydroxide solution at a constant rate over a period of 3.25 hours (11,700 s). During the addition of the sodium hydroxide, the water was removed by co-distilling with epichlorohydrin and solvent. The distillate was condensed thereby forming two distinct phases, an aqueous phase (top) and an organic, epichlorohydrin-solvent phase (bottom). The organic phase was continuously returned to the reactor. After completion of the sodium hydroxide addition, the reaction mixture was maintained at a temperature of 55° C. and a pressure of 105 mm Hg absolute for an additional 30 minutes (1800 s). The resulting glycidyl ether was then distilled under full vacuum and temperature up to 170° C. to remove all epichlorohydrin and 1-methoxy-2-hydroxy propane. The molten glycidyl ether product was diluted to 20% by weight resin concentration with a 75/25 methyl ethyl ketone/toluene solvent mixture and then washed with water several times to remove NaCl. The organic phase from the water washes was placed in a rotary evaporator under a full vacuum and a temperature of 170° C. to remove the solvent completely. A glycidyl ether product having an epoxide content of 12.21 percent, containing 36 ppm hydrolyzable chloride, 601 ppm total chloride, 46.4 weight percent bromine and a Mettler softening point of 102° C. was obtained.

B. Blending of Cresol Epoxy Novolac and Glycidyl Ether of 3,5-dibromo-2,4,6-trimethylphenol 37.7 grams (0.108 epoxy equiv.) of the glycidyl ether of 3,5-dibromo-2,4,6-trimethylphenol prepared in Example 5-A above and 164.1 g (0.82 phenolic hydroxyl equiv.) of a cresol-formaldehyde epoxy novolac resin having an average functionality of 6 were melt blended to provide a mixture with a bromine content of 8.6 weight percent.

EXAMPLE 6

Each of the products of Examples 1-5 and a control resin were formulated into an electrical encapsulating formulation. The formulations were cured at 175° C. for 4 hours (14400 s) and then tested for hydrolyzable halide content after refluxing the samples in 3N KOH in dioxane for 30 minutes (1800 s) at 90° C.; moisture absorption and dielectric constant. The encapsulating formulations are given in Table I while the results are given in Tables II, III and IV.

The properties of the cured encapsulating formulations were determined by the following methods.

HYDROLYZABLE HALIDE

The sample to be analyzed is saponified by a KOH reflux and the resulting extracted halides are titrated argentometrically by a potentiometric technique as follows. Weigh into a 250 Erlenmeyer flask 2 g of sample, add 30 ml of dioxane and stir until the sample has dissolved. Preset a heat source which will permit the sample to begin reflux in 4-6 minutes (240-360 s). Add 30 ml of 3N ethanolic KOH solution and then attach a condenser to the flask and heat to reflux with constant stirring. Reflux 30 minutes (1800 s) timed from when the firs condensed drop of liquid falls back into the flask from the condenser. Add 20 ml of 20% nitric acid in. Add 50 ml of deionized water, then cool the solution to room temperature. Calibrate the ion meter to read 0 mv against a NaCl reference solution. Titrate the sample mixture with standardized silver nitrate solution making sure that the sample mixture is spinning and the electrodes are free of resin. From the volume of titrant used, calculate the hydrolyzable chloride and hydrolyzable bromide.

MOISTURE ABSORPTION

The moisture pick-up was determined by placing weighed 3 mm×0.3 mm×160 mm cured coupons in boiling water for 20, 40, 100 and 130 hours (72,000, 144,000, 360,000 and 468,000 s). The coupons were then removed, cooled at ambient temperature (25° C.) for about 15-30 minutes (900-1800 s) and then the coupons were wiped dry and weighed.

DIELECTRIC CONSTANT

The dielectric constant was determined by the use of a Gen Rad 1689 bridge and LD-3 cell. Coupons approximately 3"×3"×⅛" (76.2 mm×76.2 mm×3.175 mm) were cut from each clear casting and measured with the Gen Rad 1689 bridge and LD-3 celll at ambient temperature. The frequency used was $1 \times 10^3$ Hz.

TABLE I

| COMPONENT | ENCAPSULATION FORMULATION | | | | | |
|---|---|---|---|---|---|---|
| | 1* | 2 | 3 | 4 | 5 | 6 |
| Epoxy Resin Type/g | Control[1]/ 201.8 | Ex. 1/ 175.9 | Ex. 2/ 166.7 | Ex. 3/ 182.7 | Ex. 4/ 201.8 | Ex. 5B/ 201.8 |
| Cresol formaldehyde Epoxy Novolac[2], g | 0 | 25.9 | 35.1 | 19.1 | 0 | 0 |
| Curing Agent[3], g | 82.7 | 82.7 | 82.7 | 82.7 | 82.7 | 82.7 |
| 2-Methyl-imidazole 10% by wt. in curing agent, g | 8.5 | 8.5 | 8.5 | 8.5 | 8.5 | 8.5 |
| Mold release agent, g | 4.0 | 4.0 | 4.0 | 4.0 | 4.0 | 4.0 |
| Epoxy Silane[5], g | 4.0 | 4.0 | 4.0 | 4.0 | 4.0 | 4.0 |
| Fused silica, g | 685.0 | 685.0 | 685.0 | 685.0 | 685.0 | 685.0 |
| Antimony Oxide, g | 10.0 | 10.0 | 10.0 | 10.0 | 10.0 | 10.0 |
| Carbon Black, g | 4.0 | 4.0 | 4.0 | 4.0 | 4.0 | 4.0 |
| % Bromine in Formulation | 1.75 | 1.75 | 1.75 | 1.75 | 1.75 | 1.75 |

TABLE II

| HYDROLYZABLE HALIDE ANALYSIS | | |
|---|---|---|
| SAMPLE NUMBER | HYDROLYZABLE CHLORIDE, PPM | HYDROLYZABLE BROMIDE, PPM |
| 1* | 240 | 180 |
| 2 | 215 | 0 |
| 3 | 235 | 0 |
| 4 | 236 | 0 |
| 5 | 240 | 0 |
| 6 | 239 | 0 |

*Not an example of the present invention.

TABLE III

| | MOISTURE ABSORPTION | | | |
|---|---|---|---|---|
| SAMPLE NUMBER | 20 Hrs. (72000 s) | 40 Hrs. (144000 s) | 100 Hrs. (360000 s) | 130 Hrs. (468000 s) |
| 1* | 0.8 | 0.867 | 0.95 | 1.0 |
| 2 | 0.75 | 0.82 | 0.9 | 0.95 |
| 3 | 0.74 | 0.81 | 0.91 | 0.96 |
| 4 | 0.8 | 0.86 | 0.95 | 1.0 |
| 5 | 0.3 | 0.35 | 0.37 | 0.4 |
| 6 | 0.75 | 0.81 | 0.89 | 0.93 |

*Not an example of the present invention.

TABLE IV

| SAMPLE NUMBER | DIELECTRIC CONSTANT |
|---|---|
| 1* | 4.67 |
| 2 | 4.61 |
| 3 | 4.12 |
| 4 | 4.05 |
| 5 | 3.83 |
| 6 | 4.60 |

*Not an example of the present invention.

We claim:

1. A mixture comprising (A) a glycidyl ether of a metabrominated monophenol and (B) a polyepoxide having an average of more than one vicinal epoxide group per molecule; wherein components (A) and (B) are employed in quantities which provide the resultant mixture with a bromine content of from about 2 to about 20 percent by weight.

2. A mixture of claim 1 wherein components (A) and (B) are employed in quantities which provide the resultant mixture with a bromine content of from about 5 to about 15 percent by weight.

3. A mixture of claim 2 wherein components (A) and (B) are employed in quantities which provide the resultant mixture with a bromine content of from about 7 to about 12 percent by weight.

4. A mixture of claim 3 wherein component (A) is a glycidyl ether of 3,5-dibromo-2,4,6-trimethylphenol, 3-bromo-2,4,6-trimethylphenol, 3,5-dibromophenol, 3-bromophenol, 3-bromo-2,4,5,6-tetramethylphenol, 3,5-dibromo-2,4,6-triethylphenol, 3-bromo-2,4,6-triethylphenol or a combination thereof and component (B) is an epoxy novolac resin or a triglycidylether of tri(hydroxyphenyl)methane.

5. A mixture of claim 4 wherein component (A) is a glycidyl ether of 3,5-dibromo-2,4,6-trimethylphenol and component (B) is a cresol-formaldehyde epoxy novolac resin.

* * * * *